United States Patent [19]

Kimble et al.

[11] Patent Number: 5,118,899
[45] Date of Patent: Jun. 2, 1992

[54] COMPOSITION OF MATTER AND METHOD OF OXIDATIVE CONVERSION OF ORGANIC COMPOUNDS THEREWITH

[75] Inventors: James B. Kimble, Bartlesville; John H. Kolts, Ochelata, both of Okla.

[73] Assignee: Phillips Petroleum Company, Bartlesville, Okla.

[21] Appl. No.: 945,129

[22] Filed: Dec. 22, 1986

[51] Int. Cl.$^5$ ................................. C07C 2/00
[52] U.S. Cl. ........................ 585/500; 585/651; 585/653; 585/654; 585/656; 585/660; 585/657; 585/658; 585/661; 585/943
[58] Field of Search ............... 585/943, 656, 660, 654, 585/651, 653, 657, 658, 661, 500

[56] References Cited

U.S. PATENT DOCUMENTS

| | | | |
|---|---|---|---|
| 2,942,960 | 6/1960 | Gerhold | 48/215 |
| 4,544,784 | 10/1985 | Sofranko et al. | 585/500 |
| 4,658,076 | 4/1987 | Kolts et al. | 585/500 |
| 4,658,077 | 4/1987 | Kolts et al. | 585/500 |
| 4,775,654 | 10/1988 | Kolt et al. | 502/226 |

FOREIGN PATENT DOCUMENTS

| | | |
|---|---|---|
| 0095665 | 4/1986 | European Pat. Off. |
| 0177327 | 4/1986 | European Pat. Off. |
| 189079A1 | 7/1986 | European Pat. Off. |

*Primary Examiner*—Patrick P. Garvin
*Assistant Examiner*—E. D. Irzinski
*Attorney, Agent, or Firm*—K. K. Brandes

[57] ABSTRACT

Compositions of matter particularly useful for the oxidative conversion of feed organic compounds to produce organic compounds include combination of Group IIA, zinc, titanium and Lanthanum Series base materials and, optionally, Group IA and/or halogen promoters. A method for the oxidative conversion of feed organic compounds to produce organic compounds, particularly methane, to higher hydrocarbons and saturated $C_2$ to $C_7$ hydrocarbons to less saturated hydrocarbons in the presence of an oxygen-containing gas is disclosed utilizing base compositions of matter.

42 Claims, No Drawings

COMPOSITION OF MATTER AND METHOD OF OXIDATIVE CONVERSION OF ORGANIC COMPOUNDS THEREWITH

The present invention relates to an improved composition of matter. In a more specific aspect, the present invention relates to a solid contact material for the oxidative conversion of feed organic compounds to product organic compounds, in the presence of a free oxygen-containing gas, and a method for such conversion.

BACKGROUND OF THE INVENTION

Numerous processes are in use and have been proposed for the conversion of organic compounds and feedstocks to more valuable organic compounds and more valuable feedstocks for use in the organic chemical and petrochemical industries, particularly organic compounds and feedstocks derived from petroleum sources.

One promising approach to such conversion has been the oxidative conversion of organic compounds to other organic compounds. However, in many cases, such oxidative conversion processes are not commercially viable, primarily because they are energy intensive, conversions of the feedstock are low, selectivity to the desired compounds is low and such processes cannot be utilized in a continuous manner. In most of such processes the feedstocks are contacted with a solid contact material. However, there is a difference of opinion among workers in the art concerning the nature of such processes, and, particularly, the function of the contact material and the manner in which such function is performed. For example, workers in the art have at one time or another suggested that the function of the contact material involves a purely physical phenomenon, an adsorption-description process, either of atomic or molecular oxygen, either on the surface or occluded within the solid material, oxidation-reduction, utilizing multivalent metals capable of oxidation-reduction, adsorption and desorption of the organic materials on the solid materials, a free radical mechanism, etc. Consequently, the solid materials utilized are referred to variously as "contact materials", "promoters", "activators" and catalysts". Accordingly, in order to avoid functional categorization, the terms "solid contact material" or "solid contact materials" will be utilized in the present invention.

Since many processes of the prior art are based on the theory that the contact materials function via adsorption-desorption of oxygen, oxidation-reduction, etc., such processes are operated in a cyclic manner by passing an oxidizing gas over the contact material, then contacting the feedstock with the oxygen-containing contact material, and, thereafter, reactivating or regenerating the contact material by again passing a free oxygen-containing gas thereover. Such processes thus require undesirably high temperatures, are energy intensive, since the exothermic and endothermic reactions occur separately, equipment costs are high, because of the necessity for rapid cycling, and the contact material's useful life is comparatively short.

From the above, it is quite clear that the suitability of contact materials for the oxidative conversion of organic compounds is unpredictable. It is, therefore, highly desirable that new and improved contact materials for such use be developed, and that improved processes utilizing such contact materials be provided, particularly processes which lower the temperatures necessary, lower the energy requirements, are capable of being carried out in a continuous manner, extend the useful life of the contact material, improve the conversion of the feedstock and improve the selectivity to the desired products.

Of the various feedstocks for the organic chemical and petrochemical industries, olefins, such as ethylene and proplyene are of particular interest and have become major feedstocks. Of these, ethylene is by far the more important chemical feedstock since the demand for ethylene feedstocks is about double that for propylene feedstocks. Consequently, there is a definite need for materials and processes for the conversion of relatively inexpensive feedstocks to ethylene. At the present time, ethylene is produced almost exclusively by the dehydrogenation or pyrolysis of ethane and propane, naphtha and, in some instances, gas oils. About 75% of the ethylene is produced at the present time by steam cracking of ethane and propane derived from natural gas, since natural gas contains from about 5 volume percent to about 60 volume percent of hydrocarbons other than methane, with the majority being ethane. However, relatively severe conditions, particularly temperatures in excess of about 1000° C., are required and, as indicated, such processes are highly energy intensive. In order to reduce the severity of the conditions, particularly temperature, numerous proposals to catalyze pyrolytic reactions have been made. While some of these processes do, in fact, reduce the severity of the conditions, the conversion of the feedstock and the selectivity to ethylene are still quite low. Of particular interest in this phase of the art, is the oxidative conversion of methane to higher hydrocarbons, particularly ethylene and ethane and, more particularly, ethylene. However, these processes have, heretofore resulted in low conversions of methane and poor selectivity to ethylene and ethane.

More recently, it has been discovered that certain solid contact materials are highly effective for the oxidative conversion of feed organic compounds to product organic compounds in the presence of a free oxygen-containing gas, particularly, for the oxidative conversion of methane to higher hydrocarbons, and the oxidative dehydrogenation of saturated $C_2$ through $C_7$ hydrocarbons to less saturated hydrocarbons. In the discussions of these contact materials, as well as the contact materials of the present invention, references are made to certain components as "base" materials, while other components are referred to as "promoters". However, it is to be understood that such designations are not to be considered as functionalizing designations, since the base materials, as well as the promoters, are all active components of the contact materials and the base materials are not inert bases or carriers for the promoting materials.

Commonly assigned U.S. patent applications Ser. No. 713, 653, Ser. No. 713,656 and Ser. No. 713,674, all filed Mar. 19, 1985, disclose compositions and contact materials for oxidative conversion in which the base materials are Group IIA metal oxides. U.S. application Ser. No. 713,673, filed Mar. 19, 1985, relates to compositions and contact materials for oxidative conversion in which the base material is zinc oxide. U.S. application Ser. No. 742,340, filed Jun. 7, 1985, utilizes a base material comprising titanium oxide. U.S. application Ser. No. 742, 337, filed Jun. 7, 1985, utilizes lanthanum and Lanthanum Series metals as base materials. Each of these base materials may be promoted with at least one Group IA metal and/or a halogen. To the extent that the contact material is prepared without a halogen, or with an inadequate amount of halogen. U.S. application Ser. No. 742,335, filed Jun. 7, 1985, discloses that the lack of halogen may be made up by at least intervally adding a halogen, or a halogen precursor, during the course of the reaction. The entire contents of each of these applications are incorporated herein by reference.

SUMMARY OF THE INVENTION

It is therefore an object of the present invention to provide an improved composition of matter and method of utilizing the same which overcomes the above and other disadvantages of the prior art. Another object of the present is to provide an improved composition of matter. Still another object of the present invention is to provide an improved contact material for the oxidative conversion of organic compounds to other organic compounds, in the presence of a free oxygen-containing gas. Another and further object of the present invention is to provide an improved method for the oxidative conversion of organic compounds to other organic compounds, in the presence of a free oxygen-containing gas. Another and further object of the present invention is to provide an improved method for the oxidative conversion of alkane hydrocarbons to other hydrocarbons, in the presence of a free oxygen-containing gas. A further object of the present invention is to provide a method for the oxidative conversion of organic compounds to other organic compounds which results in improved conversion of feedstock. Yet another object of the present invention is to provide a method for the oxidative conversion of organic compounds to other organic compounds which results in improved selectivity to desired products. A further object of the present invention is to provide a method for the oxidative conversion of organic compounds to other organic compounds which results in improved conversion of feedstock and an improved selectivity to desired products. Another and further object of the present invention is to provide a method for the oxidative conversion of organic compounds to other organic compounds which utilizes temperatures below those of known processes. A still further object of the present invention is to provide a method for the oxidative conversion of organic compounds to other organic compounds which reduces the energy requirements thereof. Another object of the present invention is to provide a method for the oxidative conversion of organic compounds to other organic compounds which can be carried out in a continuous manner. Yet another object of the present invention is to provide a method for the oxidative conversion of organic compounds to other organic compounds which extends the useful life of the contact material utilized. These and other objects of the present invention will be apparent from the following detailed description.

In accordance with the present invention, it has been discovered that combinations of the previously mentioned base materials result in compositions of matter which are at least as effective as the previously utilized contact materials for the oxidative conversion of feed organic hydrocarbons to product organic hydrocarbons in the presence of a free oxygen-containing gas, in some instances, result in higher conversions of the feed organic compounds and/or higher selectivities to desired product organic compounds and an improved useful life when utilized in an oxidative conversion reaction.

These novel compositions of matter comprise:
a solid composition of matter selected from the group consisting of:

(a) a composition consisting essentially of: (1) magnesium, (2) at least one metal selected from the group consisting of calcium, strontium and barium and (3) oxygen;

(b) a composition consisting essentially of: (1) magnesium, (2) at least one metal selected from the group consisting of calcium, strontium and barium and (3) oxygen and (4) at least one material selected from the group consisting of halogen ions and compounds containing halogen ions;

(c) a composition consisting essentially of: (1) lithium (2) magnesium, (3) at least one metal selected from the group consisting of calcium, strontium and barium and (4) oxygen;

(d) a composition consisting essentially of: (1) lithium, (2) magnesium, (3) at least one metal selected from the group consisting of calcium, strontium and barium (4) oxygen and (5) at least one material selected from the group consisting of halogen ions and compounds containing halogen ions;

(e) a composition consisting essentially of: (1) lithium (2) at least one metal selected from the group consisting of calcium, strontium and barium and (3) oxygen;

(f) a composition consisting essentially of: (1) lithium (2) at least one metal selected from the group consisting of calcium, strontium and barium (3) oxygen and (4) at least one material selected from the group consisting of halogen ions and compounds containing halogen ions;

(g) a composition consisting essentially of: (1) at least two metals selected from the group consisting of zinc, titanium and Lanthanum Series metals and (2) oxygen;

(h) a composition consisting essentially of: (1) at least two metals selected from the group consisting of zinc, titanium and Lanthanum Series metals, (2) oxygen and (3) at least one material selected from the group consisting of halogen ions and compounds containing halogen ions;

(i) a composition consisting essentially of: (1) at least one metal selected from the group consisting of Group IA metals and Group IIA metals, (2) at least one metal selected from the group consisting of zinc and titanium, (3) at least one metal selected from the group consisting of Lanthanum Series metals and (4) oxygen;

(j) a composition consisting essentially of: (1) at least one metal selected from the group consisting of Group IA metals and Group IIA metals, (2) at least one metal selected from the group consisting of zinc and titanium, (3) at least one metal selected from the group consisting of Lanthanum Series metals, (4) oxygen and (5) at least one material selected from the group consisting of halogen ions and compounds containing halogen ions;

(k) a composition consisting essentially of: (1) at least one metal selected from the group consisting of Group IA metals and Group IIA metals, (2) zinc, (3) titanium and (4) oxygen;

(l) a composition consisting essentially of: (1) at least one metal selected from the group consisting of Group IA metals and Group IIA metals, (2) zinc, (3) titanium, (4) oxygen and (5) at least one material selected from the group consisting of halogen ions and compounds containing halogen ions;

(m) a composition consisting essentially of: (1) at least one metal selected from the group consisting of Group IA metals and Group IIA metals, (2) lanthanum, (3) at least one metal selected from the group consisting of Lanthanum Series metals other than lanthanum, and (4) oxygen;

(n) a composition consisting essentially of: (1) at least one metal selected from the group consisting of Group IA metals and Group IIA metals, (2) lanthanum, (3) at least one metal selected from the group consisting of Lanthanum Series metals other than lanthanum, (4) oxygen and (5) at least one material selected from the group consisting of halogen ions and compounds containing halogen ions;

(o) a composition consisting essentially of: (1) at least one metal selected from the group consisting of Group IIA metals, (2) at least one metal selected from the group consisting of zinc and lanthanum and (3) oxygen;

(p) a composition consisting essentially of: (1) at least one metal selected from the group consisting of Group IIA metals, (2) at least one metal selected from the group consisting of zinc and lanthanum (3) oxygen and (4) at least one material selected from the group consisting of halogen ions and compounds containing halogen ions;

(q) a composition consisting essentially of: (1) at least one metal selected from the group consisting of Group IIA metals, (2) at least one metal selected from the group consisting of Group IIA metals, (3) at least one metal selected from the group consisting of zinc and lanthanum and (4) oxygen; and (r) a composition consisting essentially of: (1) at least one metal selected from the group consisting of Group IIA metals, (2) at least one metal selected from the group consisting of Group IIA metals, (3) at least one metal selected from the group consisting of zinc and lanthanum, (4) oxygen and (5) at least one material selected from the group consisting of halogen ions and compounds containing halogen ions.

In accordance with another aspect of the present invention, these solid compositions of matter are adapted to convert feed organic compounds to product organic compounds in the presence of a free oxygen-containing gas and a method for converting feed organic compounds to product organic compounds in the presence of a free oxygen-containing gas are disclosed utilizing these solid compositions of matter as solid contact materials.

DESCRIPTION OF THE PREFERRED EMBODIMENTS

The Group IA metals are preferably selected from the group consisting of lithium, sodium and potassium.

The Group IIA metals are preferably selected from the group consisting of magnesium, calcium, strontium and barium as specified. The Lanthanum Series metals other than lanthanum, are preferably cerium, praseodymium, samarium and terbium.

The halogen is preferably chlorine. To the extent that the contact material is prepared without a halogen, and an effective amount of the halogen is desired, the halogen may be supplied by disposing the contract material in the reaction zone and contacting the contact material with a halogen, or a halogen precursor, such as methyl chloride, before the feed organic compounds and the oxygen-containing gas flow are started, or intervally after the flow of feed organic compounds and free oxygen-containing gas are initiated and the reaction is underway. Likewise, to the extent that the contact material initially contains a halogen in an amount less than an effective amount or the amount desired, or the content of halogen becomes depleted, the halogen may be increased by at least intervally adding a halogen, or a halogen precursor, to the feed organic compounds and free oxygen-containing gas during the course of the reaction.

The components of the composition of matter or contact material of the present invention, with the exception of the halogen, are present in the form of their oxides.

When the term "effective amount" is utilized with reference to the composition of matter or the contact materials herein, this term is meant to include more than an insignificant amount and, thus, a small amount sufficient to effect the function of the composition of matter for the purpose for which it is utilized. Consequently, the above compositions of matter or contact materials may contain from an effective amount of a particular component to near 100 percent, so long as an effective amount of each of the other components is present. Consequently, any of the components of the composition of matter or contact material may be present in amounts between about 0.05 weight percent to 99.95 weight percent, expressed in terms of the elemental component, based on the total weight of the active components of the composition of matter or contact material. However, from a practical standpoint, the Group IA metal promoters are present in an amount between about 0.1 and 50 weight percent, expressed in terms of the elemental metal, based on the total weight of the active components of the contact material. Preferably, the amount of Group IA metal promoter is between about 0.5 weight percent and 15 weight percent, and still more preferably, between about 0.1 weight percent and about 5 weight percent.

Likewise, the halogen, when present, is preferably utilized in amounts between about 0.1 and 5 weight percent, expressed in terms of elemental halogen. The remainder of the compositions of matter or contact materials are made up of the combinations of the base materials. As is quite evident, the ratio of one base material to another may vary over a very wide range, for example, between about 0.05 and 99.95 to 1. In order to take advantage of the second or additional base components, the ratio is preferably between about 0.3 and 3 to 1.

The above-mentioned components can be mixed with or deposited on an "inert supported material" adapted to harden or support the active materials. The term "inert support material" when utilized in this context is meant to include any material which does not react with or exchange ions with the active components, has no significant functional effect on the production of desired or undesired products in the process for which the solid contact material is utilized and functions only as a hardening agent or support for the active components. Where such solid support material is utilized, the weight of such solid support material is not included in determining the relative weights of the active components.

The Group IA metal, Group IIA metal, zinc, titanium, Lanthanum Series metals and halogen can be derived from any suitable source of such materials, such as compounds of the elements in the form of carbonates, hydroxides, oxides, nitrates, octoates, chlorides, etc. The compositions of matter and contact materials can be prepared by any suitable method known in the art for the preparation of such materials in solid form. Particularly effective techniques are those utilized for the preparation of solid catalysts. Conventional methods include coprecipitation from an aqueous, an organic or a combination solution-dispersion, impregnation, dry mixing, wet mixing or the like, alone or in various combinations. In general, any method can be used which provides compositions of matter containing the prescribed components in effective amounts. For example, the compositions may be produced by mixing compounds of the elements in a blender with enough water to form a thick slurry. The slurry can then be dried, usually at a temperature sufficient to volatilize the water or other carrier, such as about 220° F. to about 450° F. Alternatively, pellets of one or more oxides can be impregnated with an aqueous solution of a compound of another component and dried. In all cases, irrespective of how the components are combined, and irrespective of the source of the metal or halide, the dried composition is calcined in the presence of a free oxygen-containing gas, usually at temperatures between about 700° F. and about 1500° F. for from 1 to about 24 hours. While the exact form of the metals in the resultant composition and contact materials is not known, it is believed that all components are present as their oxides except the halogen which is present in the form of a halide.

These compositions of matter and contact materials are particularly useful for the oxidative conversion of feed organic compounds to product organic compounds, in the presence of a free oxygen-containing gas. Processes of this character include the oxidative dehydrogenation of hydrocarbons, particularly alkanes having 2 to 7 carbon atoms, to other hydrocarbons, particularly ethylene, the oxidative methylation of toluene, in the presence of methane, to ethyl benzene and styrene, the oxidative conversion of toluene to stilbene, the oxidative methylation of acetonitrile, in the presence of methane, to acrylonitrile and $C_2+$ hydrocarbons and the oxidative methylation of other hydrocarbons. The compositions of matter and contact materials of the present invention are particularly useful for the oxidative conversion of methane to higher hydrocarbons, particularly the oxidative conversion of methane to ethylene, in the presence of a free oxygen-containing gas.

The conditions of operation of such processes for the oxidative conversion of feed organic compounds to product organic compounds can vary over a wide range. Such conditions are either known to those skilled in the art or can be readily optimized by one skilled in the art by simple, conventional experiments.

Since the composition of matter and contact materials of the present invention are highly effective for the oxidative conversion of methane to higher hydrocarbons, particularly ethylene and ethane, and this process is of great value, the conversion of feed organic materials to product organic materials will be illustrated and exemplified by such methane conversion.

In accordance with most previous theories of the function and operation of contact materials for the oxidative conversion of methane to higher hydrocarbons, and particularly ethylene and ethane, the reaction has been carried out in the absence of a free oxygen-containing gas, with the oxygen theoretically being supplied by the contact material. As a result, the most utilized modes of operation have included treating the contact material with a free oxygen containing gas, such as oxygen or air, for a period of time sufficient to produce a reducible oxide of a multivalent metal, thereafter, contacting methane with the reducible metal oxide and, thereafter, treating the metal oxide with a free oxygen-containing gas to "regenerate" the same. Similarly, certain contact materials are contacted with a free oxygen-containing gas to cause adsorption of oxygen on the contact material, methane is, thereafter, contacted with the contact material containing adsorbed oxygen and, thereafter, the contact material is again treated with a free oxygen-containing gas. In both instances, the contact material, after treatment with a free oxygen-containing gas, is usually purged with an inert gas, such as nitrogen, to remove excess oxygen which has not reacted with or been adsorbed on the contact material. Consequently, several techniques have been followed, including, carrying out the contact with methane and the contact with a free oxygen-containing gas in separate reaction chambers or sequentially passing a free oxygen-containing gas, a purge gas and methane through the contact material in a single reaction vessel. The disadvantages of either of these procedures will be evident to one skilled in the art.

In contrast to these prior art techniques, the method of the present invention is carried out by contacting methane with a contact material, in the presence of a free oxygen-containing gas.

In addition to methane, the hydrocarbon feedstock, employed in the method of the present invention, may contain other hydrocarbon or non-hydrocarbon components. The presence of ethane, propane and the like is not detrimental. It has been found that carbon dioxide and water are not detrimental, since they are most often products of the process. It has also been found that inert gases, such as nitrogen, helium and the like are not detrimental. Consequently, the method of the present invention can effectively utilize any conventional natural gas. To the extent that significant amounts of hydrogen sulfide are present in the natural gas, it is desirable to first remove the hydrogen sulfide, since it is believed that excessive amounts of this material can be detrimental to the method. Accordingly, a relatively inexpensive source of methane, namely natural gas, can be employed without expensive separation or processing of the components thereof, with the exception of the relatively inexpensive removal of excess amounts of hydrogen sulfide. Other sources of methane or methane-containing gases can also be utilized.

The free oxygen-containing gas may be any suitable oxygen-containing gas, such as oxygen, oxygen-enriched air or air. The method of the present application has been effectively carried out utilizing air as a source of oxygen.

When utilized in the present invention, the term "diluent gas" is meant to include any gaseous material present in the methane-containing gas, the free oxygen-containing gas or in the form of an added gas which is essentially inert with respect to the oxidative conversion of methane and, thus, does not significantly decrease the conversion of methane and/or the selectivity to the production of higher hydrocarbons.

The volumetric ratio of methane to free oxygen should be in excess of about 1/1, preferably it is between about 1/1 and about 30/1 and still more preferably between about 4/1 and about 15/1. It has been found that a ratio of methane to free oxygen of at least about 1/1 is necessary, in accordance with the present invention, in order to obtain maximum conversion of methane and high selectivity to higher hydrocarbons, particularly ethylene.

In the present invention, it has been found that the method can be carried out between two extremes, namely, low conversion of methane/high selectivity to higher hydrocarbons, particularly ethylene, and high conversion of methane/low selectivity to the higher carbons, particularly ethylene. The process parameters (space velocity, temperature, and reactant partial pressure) can, to some extent, be used to control the reaction at the desired point between these two limits. Consequently, the reaction conditions may vary between broad limits.

The temperature is preferably about at least about 500° C. and will generally vary between about 500° C. and about 1500° C. However, in order to obtain high conversions of methane and high selectivities to ethylene and ethane, the temperature is preferably between about 500° C. and about 900° C. and most desirably between about 600° C. and about 800° C.

It has also been found that, as the partial pressure of oxygen is increased, the selectivity to higher hydrocarbons decreases and the selectivity to carbon dioxide increases and vice versa. Total pressures may vary anywhere from around 1 atmosphere to about 1500 psi but are preferably below about 300 psi and ideally below about 100 psi.

Methane flow rates can also vary over a wide range, for example, from 0.5 to 100 cubic centimeters per minute per cubic centimeter of contact material. Preferably, however, the rate is between about 1.0 and about 75 cubic centimeters per minute per cubic centimeter of contact material.

The total flow velocities of all gaseous materials, including diluents, through a fixed bed reactor, may be at any rate effective for the oxidative conversion reaction. For example, from 50 to 10,000 GHSV and preferably from 500 to 5000 GHSV.

In addition to the high conversion of methane and high selectivity to ethylene and ethane, attainable in accordance with the present invention, the contact materials are not readily poisoned and will tolerate the presence of water, carbon dioxide, carbon monoxide and the like. In addition, the contact materials appear to be long lived, with no noticeable deactivation problems. Concomitantly, the process can be carried out continuously in fixed, moving, fluidized, ebullating or entrained bed reactors.

The following examples illustrate the nature and advantages of the present invention.

In the following example, the oxides of the base materials were mixed together as a paste to produce a composite base material having the specified weight percent of the metal indicated. Thereafter, lithium carbonate was added to produce a mixture having 3 percent of lithium, expressed in terms of the metal, as a promoter. The paste was then calcined at a temperature of about 800° C. During calcination, the carbonate was, of course, converted to lithium oxide. Contact materials 10 through 12 were prepared by forming a mixture of paste, as previously, extruding the physical mixture and thereafter calcining at 800° C. In the preparation of contact material 12, a small amount of graphite was utilized to aid in extrusion and lubricate the die. The contact materials were then utilized to convert methane to higher hydrocarbons, particularly ethylene and ethane. The reaction was carried out at the temperature specified, at a GHSV of 500 and a methane/nitrogen diluent/oxygen ratio of 5/4/1.

TABLE

| Run No. | Wt. % Metal | Temp (°C.) | Conv. (%) | Selectivity (%) $C_2=$ | $C_2$ | $C_2=/C_2$ |
|---|---|---|---|---|---|---|
| 1 | Li/Mg 3/100 | 668 705 | 10 21 | 38 26 | 19 35 | 2.00 0.74 |
| 2 | Li/Mg/Zn 3/75/25 | 675 705 | 19 23 | 27 33 | 27 24 | 1.00 1.38 |
| 3 | Li/Mg/Zn 3/50/50 | 675 704 | 17 22 | 26 34 | 31 26 | 0.84 1.31 |
| 4 | Li/Mg/Zn 3/25/75 | 705 721 | 16 28 | 27 31 | 33 29 | 0.82 1.07 |
| 5 | Li/Ca 3/100 | 705 750 | 19 23 | 29 18 | 30 39 | 0.87 0.46 |
| 6 | Li/Ca/Zn 3/75/25 | 705 733 | 21 26 | 34 33 | 25 17 | 1.36 1.94 |
| 7 | Li/Ca/Zn 3/50/50 | 705 720 | 20 23 | 30 33 | 26 20 | 1.15 1.65 |
| 8 | Li/Ca/Zn 3/25/75 | 705 720 | 20 23 | 28 32 | 26 22 | 1.08 1.45 |
| 9 | Li/Zn 3/100 | 700 715 | 9 11 | 44 40 | 24 30 | 1.83 1.33 |
| 10 | Li/Mg/Zn 3/25/75 | 800 | 19 | 38 | 31 | 1.23 |
| 11 | Li/Mg/Zn 3/95/5 | 800 | 23 | 37 | 29 | 1.28 |
| 12 | Li/Mg/Zn 3/75/25 | 800 | 21 | 37 | 29 | 1.28 |

It is also to be observed that the contact materials containing mixed bases can be essentially tailored to survive use in a particular type of reactor, for example, a fixed bed reactor, a fluidized bed reactor, and the like. For example, magnesium oxide and calcium oxide are relatively soft and, at times, cause difficulties in testing even in laboratory-size equipment. On the other hand, zinc oxide is extremely hard and is difficult to form into particles suitable for testing. However, if the two or mixed as indicated herein, materials that can be readily formed by commercial extrusion equipment which have sufficient strength to withstand use in conventional commercial equipment. For example, contact material 10 had a crush strength of 50 to 74 pounds; 11 had a crush strength of 96 pounds, and 12 had a crush strength of 57 pounds. These crush strengths are easily high enough to survive in a fixed bed type of reactor.

Conditions for the oxidative dehydrogenation of $C_2$ to $C_7$ hydrocarbons can also vary over the same broad ranges useful for the oxidative conversion of methane to higher hydrocarbons and can be optimized by one skilled in the art by conventional, routine experimentation.

As a general rule, the conditions for the oxidative dehydrogenation of $C_2$ to $C_7$ hydrocarbons will fall within the lower part of the ranges previously specified for the oxidative conversion of methane to higher hydrocarbons. For example, a GHSV of 100 to 1000, and preferably 400 to 500, and a hydrocarbon to oxygen ratio of 1/1 to 30/1, and preferably 1/1 to 3/1, a temperature of 600° C. to 775° C., and preferably 650° C. to 725° C., and a pressure of 0.5 to 10 atmospheres, and preferably 1 atmosphere, are highly effective.

While specific materials, conditions of operation, modes of operation and equipment have been referred to herein, it is to be recognized that these and other specific recitals are for illustrative purposes and to set forth the best mode only and are not to be considered limiting.

That which is claimed:

1. A method for the oxidative conversion of a feed consisting essentially of methane to product organic compounds comprising higher hydrocarbons, comprising:

contacting said feed organic compounds and a free oxygen-containing gas with a solid material selected from the group consisting of:

(A) a contact material consisting essentially of: (1) at least one metal selected from the group consisting of Group IIA metals, (2) zinc, (3) titanium, (4) lanthanum and (5) oxygen;

(B) a contact material consisting essentially of: (1) at least one metal selected from the group consisting of Group IA metals, (2) at least one metal selected from the group consisting of Group IIA metals, (3) zinc, (4) titanium, (5) lanthanum and (6) oxygen;

(C) a contact material consisting essentially of: (1) at least one metal selected from the group consisting of Group IIA metals, (2) zinc, (3) titanium, (4) lanthanum, (5) oxygen and (6) at least one ion selected from the group consisting of halogen ions;

(D) a contact material consisting essentially of: (1) at least one metal selected from the group consisting of Group IIA metals, (2) at least one metal selected from the group consisting of Group IIA metals, (3) zinc, (4) titanium, (5) lanthanum, (6) oxygen and (7) at least one ion selected from the group consisting of halogen ions;

(E) a contact material consisting essentially of: (1) at least one metal selected from the group consisting of Group IIA metals, (2) zinc, (3) titanium, and (4) oxygen;

(F) a contact material consisting essentially of: (1) at least one metal selected from the group consisting of Group IA metals, (2) at least one metal selected from the group consisting of Group IIA metals, (3) zinc, (4) titanium, and (5) oxygen;

(G) a contact material consisting essentially of: (1) at least one metal selected from the group consisting of Group IIA metals, (2) zinc, (3) titanium, (4) oxygen and (5) at least ion selected from the group consisting of halogen ions;

(H) a contact material consisting essentially of: (1) at least one metal selected from the group consisting of Group IIA metals, (2) at least one metal selected from the group consisting of Group IIA metals, (3) zinc, (4) titanium, (5) oxygen and (6) at least one ion selected from the group consisting of halogen ions;

(I) a contact material consisting essentially of: (1) at least one metal selected from the group consisting of Group IIA metals, (2) zinc and (3) oxygen;

(J) a contact material consisting essentially of: (1) at least one metal selected from the group consisting of Group IIA metals, (2) zinc, (3) lanthanum and (4) oxygen;

(K) a contact material consisting essentially of: (1) at least one metal selected from the group consisting of Group IIA metals, (2) zinc, (3) oxygen and (4) at least one ion selected from the group consisting of halogen ions;

(L) a contact material consisting essentially of: (1) at least one metal selected from the group consisting of Group IIA metals, (2) zinc, (3) lanthanum, (4) oxygen and (5) at least one ion selected from the group consisting of halogen ions;

(M) a contact material consisting essentially of: (1) at least one metal selected from the group consisting of Group IA metals, (2) at least one metal selected from the group consisting of Group IIA metals, (3) zinc and (4) oxygen;

(N) a contact material consisting essentially of: (1) at least one metal selected from the group consisting of Group IA metals, (2) at least one metal selected from the group consisting of Group IIA metals, (3) zinc, (4) lanthanum and (5) oxygen;

(O) a contact material consisting essentially of: (1) at least one metal selected from the group consisting of Group IA metals, (2) at least one metal selected from the group consisting of Group IIA metals, (3) zinc, (4) oxygen and (5) at least one ion selected from the group consisting of halogen ions; and (P) a contact material consisting essentially of: (1) at least one metal selected from the group consisting of Group IA metals, (2) at least one metal selected from the group consisting of Group IIA metals, (3) zinc, (4) lanthanum, (5) oxygen and (6) at least one ion selected from the group consisting of halogen ions;

under oxidative conversion condition sufficient to convert said feed to said product organic compounds.

2. A process in accordance with claim 1, wherein the level of said at least one Group IA metal, when present, is about 0.5 to about 15 weight-%.

3. A process in accordance with claim 1, wherein the level of said halogen, when present, is about 0.1 to about 5 weight-%.

4. A process in accordance with claim 1 employing contact material (A).

5. A process in accordance with claim 1 employing contact material (B).

6. A process in accordance with claim 1 employing contact material (C).

7. A process in accordance with claim 6, wherein said halogen is chlorine.

8. A process in accordance with claim 1 employing contact material (D).

9. A process in accordance with claim 8, wherein said halogen is chlorine.

10. A process in accordance with claim 1 employing contact material (E).

11. A process in accordance with claim 1 employing contact material (F).

12. A process in accordance with claim 1 employing contact material (G).

13. A process in accordance with claim 12, wherein said halogen is chlorine.

14. A process in accordance with claim 1 employing contact material (H).

15. A process in accordance with claim 14, wherein said halogen is chlorine.

16. A process in accordance with claim 1 employing contact material (I).

17. A process in accordance with claim 1 employing contact material (J).

18. A process in accordance with claim 1 employing contact material (K).

19. A process in accordance with claim 18, wherein said halogen is chlorine.

20. A process in accordance with claim 1 employing contact material (L).

21. A process in accordance with claim 20, wherein said halogen is chlorine.

22. A process in accordance with claim 1 employing contact material (M).

23. A process in accordance with claim 1 employing contact material (N).

24. A process in accordance with claim 1 employing contact material (O).

25. A process in accordance with claim 24, wherein said halogen is chlorine.

26. A process in accordance with claim 1 employing contact material (P).

27. A process in accordance with claim 26, wherein said halogen is chlorine.

28. A process in accordance with claim 1, wherein said oxidative conversion conditions comprise a temperature in the range of from about 500° C. to about 900° C. and a volumetric ratio of methane to free oxygen in the range of from about 1/1 to about 30/1.

29. A process for the oxidative conversion of a feed consisting essentially of methane to product organic compounds comprising higher hydrocarbons which comprises: contacting said feed organic compounds and a free oxygen containing gas with a solid contact material consisting essentially of (1) at least one Group IIA metal selected from the group consisting of magnesium, calcium, strontium and barium, (2) zinc and (3) oxygen; under oxidative conversion conditions sufficient to convert said feed to product organic compounds.

30. A process in accordance with claim 28, wherein said contact material consists essentially of magnesium oxide and zinc oxide.

31. A process in accordance with claim 28, wherein said contact material consists essentially of calcium oxide and zinc oxide.

32. A process in accordance with claim 28, wherein said oxidative conversion conditions comprise a temperature in the range of from about 500° C. to about 900° C. and a volumetric ratio of methane to free oxygen in the range of from about 1/1 to about 30/1.

33. A process in accordance with claim 32, wherein said temperature is about 600° C.–800° C. and said volumetric ratio is about 4/1 to about 15/1.

34. A process for the oxidative conversion of a feed consisting essentially of methane to product organic compounds comprising higher hydrocarbons which comprises: contacting said feed and a free oxygen-containing gas with a solid contact material consisting essentially of (1) at least one Group IA metal selected from the group consisting of lithium, sodium, and potassium, (2) at least one Group IIA metal selected from the group consisting of magnesium, calcium, strontium, and barium, (3) zinc and (4) oxygen; under oxidative conversion conditions sufficient to convert said feed to product organic compounds.

35. A process in accordance with claim 37, wherein the content of said at least one Group I metal in said contact material is about 0.5–15 weight percent.

36. A process in accordance with claim 34, wherein said at least one Group IA metal is lithium.

37. A process in accordance with claim 34, wherein said contact material consists essentially of lithium oxide, magnesium oxide and zinc oxide.

38. A process in accordance with claim 36, wherein the lithium content in said contact material is about 0.5–15 weight-%.

39. A process in accordance with claim 34, wherein said contact material consists essentially of lithium oxide, calcium oxide and zinc oxide.

40. A process in accordance with claim 39, wherein the lithium content in said contact material is about 0.5–15 weight-%.

41. A process in accordance with claim 34, wherein said oxidative conversion conditions comprise a temperature in the range of from about 500° C. to about 900° C. and a volumetric ratio of methane to free oxygen in the range of from about 1/1 to about 30/1.

42. A process in accordance with claim 41, wherein said temperature is about 600° C.–800° C. and said volumetric ratio is about 4/1–15/1.

* * * * *

UNITED STATES PATENT AND TRADEMARK OFFICE
CERTIFICATE OF CORRECTION

PATENT NO. :   5,118,899
DATED      :   June 2, 1992
INVENTOR(S) :  James B. Kimble and John H. Kolts It is certified that error appears in the above-identified patent and that said Letters Patent is hereby corrected as shown below:

Claim 1, Column 11, lines 22 and 43, delete "IIA" and substitute --- IA --- therefor.

Claim 29, Column 13, line 22, delete "organic compounds" after "feed".

Claims 30, 31 and 32, Column 13, delete "28" each occurrence after "claim" and substitute --- 29 --- therefor.

Claim 35, Column 14, line 16, delete "37" after "claim" and substitute --- 34 --- therefor.

Signed and Sealed this

Twenty-fourth Day of August, 1993

*Attest:*

BRUCE LEHMAN

*Attesting Officer*   *Commissioner of Patents and Trademarks*